United States Patent [19]

Probst et al.

[11] Patent Number: 4,557,376
[45] Date of Patent: Dec. 10, 1985

[54] SELF ACTIVATING AMALGAM CAPSULE

[75] Inventors: Robert L. Probst; William A. Groves, both of Ann Arbor, Mich.

[73] Assignee: Sybron Corporation, Rochester, N.Y.

[21] Appl. No.: 501,209

[22] Filed: Jun. 6, 1983

Related U.S. Application Data

[63] Continuation-in-part of Ser. No. 307,992, Oct. 2, 1981.

[51] Int. Cl.[4] .............................................. B65D 81/32
[52] U.S. Cl. .................................. 206/219; 206/63.5;
206/220; 366/602
[58] Field of Search ..................... 206/63.5, 219, 220,
206/221, 568; 215/DIG. 8; 128/272; 366/602

[56] References Cited

U.S. PATENT DOCUMENTS

| 2,647,638 | 8/1953 | Shore | 210/196 |
|---|---|---|---|
| 2,687,130 | 8/1954 | Cohen | 128/272 |
| 3,139,180 | 6/1964 | Kobernick | 206/221 |
| 3,785,481 | 1/1974 | Allet-Coche | 206/219 |
| 3,792,530 | 2/1974 | Smith | 32/54 |
| 3,831,742 | 8/1974 | Gardella et al. | 206/219 |
| 3,917,062 | 11/1975 | Winters | 206/219 |
| 4,182,447 | 1/1980 | Kay | 206/220 |
| 4,185,740 | 1/1980 | Perfect | 206/220 |

FOREIGN PATENT DOCUMENTS

| 5674880 | 10/1979 | Australia . |
| 81091 | 4/1898 | Canada . |
| 1504122 | 10/1967 | France . |
| 7904822 | 2/1981 | Sweden . |

Primary Examiner—Joseph Man-Fu Moy
Assistant Examiner—David T. Fidei
Attorney, Agent, or Firm—Robert A. Gerlach; Joseph C. MacKenzie; Frank Pincelli

[57] ABSTRACT

A two-piece, two chamber self-activating capsule having mercury in one chamber and metal powder in the other. In use, the capsule is shaken and the resulting force due to the inertia of the mercury forces its way through a normally-closed valve into the metal powder chamber, whereby the metal powder and mercury become triturated by the shaking and form dental amalgam for filling teeth. A pestle may be included to facilitate mingling and triturating the amalgam components.

10 Claims, 8 Drawing Figures

SELF ACTIVATING AMALGAM CAPSULE

RELATED APPLICATION

This is a continuation-in-part of our prior application, Ser. No. 307,992, similarly-entitled, and filed Oct. 2, 1981.

FIELD OF THE INVENTION

The field of the invention is dentistry, in particular, two-piece, two chamber, self-activating capsules for storing dental amalgam components in unmixed condition until use, wherein the capsules also provide for mingling the components and triturating them together.

DESCRIPTION OF THE PRIOR ART

Two-piece, two-chamber capsules for containing amalgam components, and having one-step charging, are disclosed in the following U.S. patents and prior French patent publications:

| | |
|---|---|
| Winters | U.S. Pat. No. 3,917,062 |
| Biondo et al | U.S. Pat. No. 4,142,629 |
| Raulo (France) | U.S. Pat. No. 1,056,507 |
| Rimbaud | U.S. Pat. No. 2,470,739 |

Two-chamber capsules requiring pestles and/or partitions between the chambers, but not having one-step charging, are disclosed in the following U.S. patents:

| | |
|---|---|
| Horton | U.S. Pat. No. 3,275,302 |
| Allet-Coche | U.S. Pat. No. 3,796,303 |
| Allet-Coche | U.S. Pat. No. 3,809,225 |
| Kay | U.S. Pat. No. 4,182,447 |
| Perfect | U.S. Pat. No. 4,185,740 |

Horton, Kay and Perfect describe self-activation in their capsules. The FIG. 2 species of Raulo is also described as having self-activation.

None of these prior art capsules combine two-piece construction, one-step charging and self-activation, but it is the overall object of this invention to provide a novel capsule of that description.

Further, another object of this invention is to provide a new and improved self-activating capsule. More particularly, it is also an object of our invention to provide a new self-activating, two-piece capsule.

Yet another object of our invention is to provide a novel capsule capable of self-activation with or without the use of a pestle therein. More particularly, it is also an object of our invention to provide a capsule having a pestle therein of novel form.

Other objects of our invention will be evident from the detailed description, infra, as well as from the claims appended hereto.

SUMMARY OF THE INVENTION

Our invention provides a self-activating, two-piece, two chamber capsule containing the components of dental amalgam. It is also a two-piece structure requiring no movable, slidable or frangible partition. Also, while the capsule needs no pestle one may be provided, if desired.

Communication between the chambers is controlled by a normally-closed valve. When the capsule is shaken in a manner normally used for trituration, the mercury's inertia opens the valve, so that the mercury passes into the chamber which contains the metal powder, and is triturated therewith to form the usual amalgam for filling teeth.

In the preferred form, our invention provides self-activation and one-step charging in a two-piece, two-chamber capsule wherein the one-way valve comprises a portion of each piece of the capsule structure, and both chambers are mainly in one of the pieces. Both chambers open separately to the exterior, and the other piece closes both such openings with the aforesaid portions then normally preventing communication between said chambers. In this arrangement, one-step charging is provided, by which we mean that appropriate quantities of metal powder and alloy can be poured simultaneously into their respective chambers via said openings, after which the two pieces can be assembled without further manipulations. This is a one-step procedure because the piece having the openings needs only to be oriented properly (chamber openings at the highest point), and after the mercury and metal powder are in place, it is then only necessary to put the other piece in place.

In use by the dentist, our capsule will be taken from a box or other storage means and placed in an amalgamator and shaken thereby for a predetermined time suitable for reducing the separate components to an amalgam of properties appropriate for filling teeth. Immediately, the shaking begins, the aforesaid valve opens and admits the mercury to the chamber containing the metal powder. At this point, the amalgamating process occurs just as in prior art capsules, with or without pestle, except that if a pestle is present, it can materially shorten trituration time. When used, the pestle may be added to the capsule along with the alloy powder, when charging the capsule.

BRIEF DESCRIPTION OF THE DRAWING

N.B. FIGS. 2 through 8 are also to scale and larger than life, but less exaggerated in dimensions than FIG. 1.

DETAILED DESCRIPTION

Figure 1:
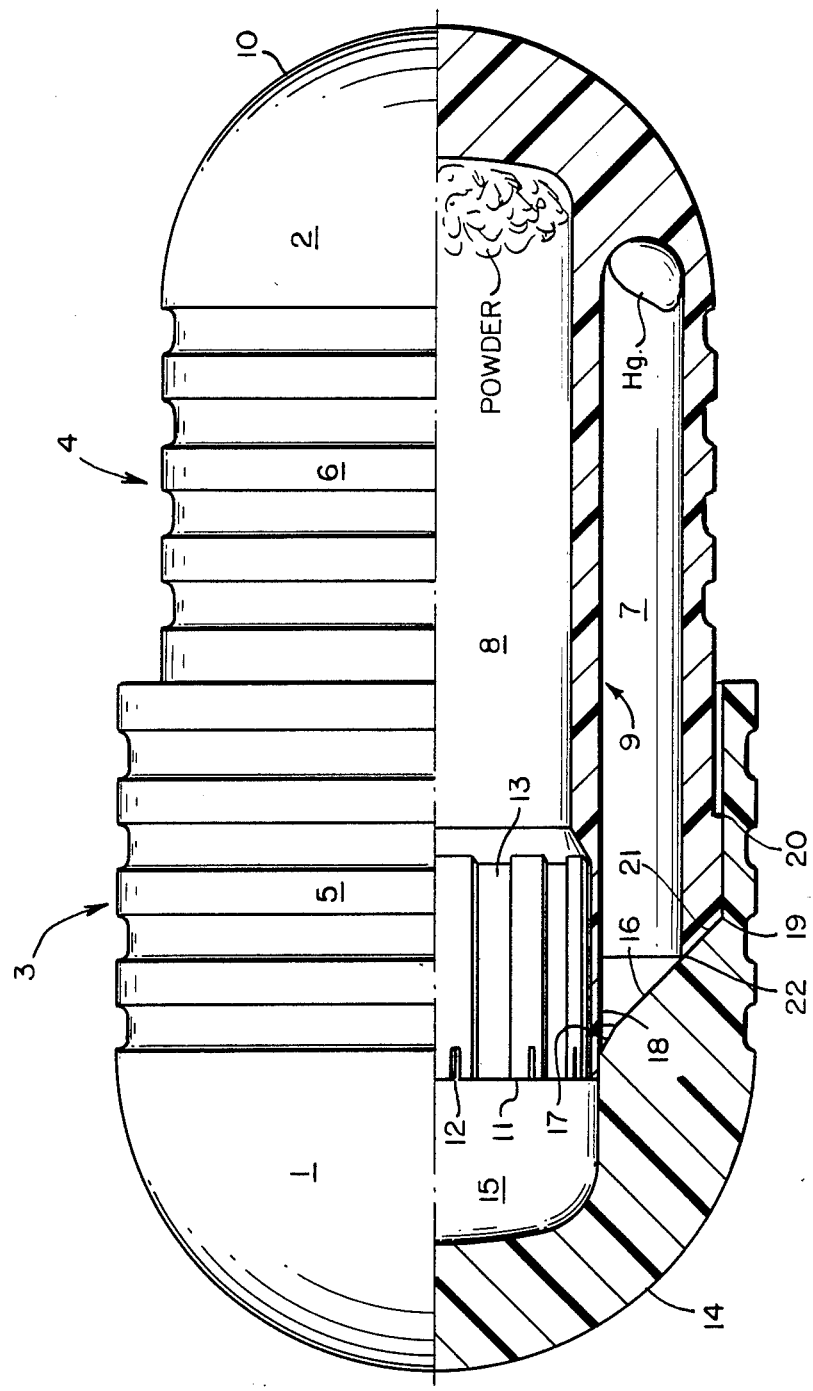
FIG. 1, is a partly-sectioned elevation of the assembled capsule according to our invention. The figure is to scale of an actual working example, but rather larger than life.
Figure 6:
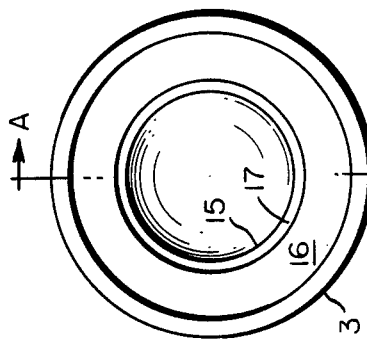
FIG. 6 is a right-ended view of the capsule section of FIGS. 2 and 3.

Referring to FIG. 1, the capsule according to the invention, and as seen for the top half of the Figure, is a generally-cylindrical two-piece structure consisting of round-ended sections 1 and 2 having overlapping circularly right-cylindrical portions 3 and 4, which are ribbed, as indicated at 5 and 6 in order to facilitate handling.

The lower half of FIG. 1, which is a section on the vertical plane containing the cylinder axis of portions 3 and 4 show section 2 as having chambers 7 and 8 therein. While not shown, in the final products, there would be small quantity of mercury in chamber 7, and a small quantity of metal powder, and the relative proportions would be those suitable for tooth-filling. Optionally, a pestle P is also provided in chamber 8.

Conveniently, chamber 7 is annular, being formed by concentric circularly right-cylindrical section 9 which is integral to and located coaxially of portion 4 of the section 2, and, along with chamber 8, is closed at one end by the rounded end 10 of piece 2. Section 9 forms a common wall of chamber 7 and 8.

The other, open end 11 of section 9 is annular, and at that end the material of section 9 rather thinner-walled than that of its intermediate portion, and there are notches 12 and channels 13 in said end 11.

Section 1 has a rounded end 14 corresponding to end 10 of section 2, having an circularly right-cylindrical internal bore 15 of less internal diameter than the portion 3 and joining thereto via the bore's frusto-conical transition 16. The right hand open end of portion 3 sealingly receives therein the left hand open end of portion 4.

At the same time, the cylindrical portion of bore 15 sealingly receives the left hand open end of section 9.

It will be observed that once the sections have been manufactured, as by molding from suitable plastic, charging and assembly consists of supporting section 1 with its axis vertical and on its rounded end, thereby allowing separate quantities of mercury and metal to be dropped, separately but simultaneously, into respective chamber 7 and 8. If pestle P is to be provided, at this time it would be dropped into chamber 8, also. That done, all that must then follow is putting section 1 over the open end of section 2 in order to seal the amalgam components into their separate chamber. After is, there is no further manipulation of the two sections or of their mutual relationship, until the components therein have become amalgam, and the dentist has to separate the sections in order to get at the amalgam.

As will be seen from FIG. 1, there is an annular sealing area on the inside surface of bore 15, due to continuous contact therewith of the outer circumferential area of the open end 11 of section 9. The width of the sealing area is the distance between points 17 and 18.

As similar annular sealing area extends circumferentially of the exterior surface of the open end of portion 4, the width of this area being the distance between points 19 and 20. In addition, a third sealing area defined by the frusto-conical end face 21 of portion 4 contacting the surface of correspondingly-shaped transition portion 16 continuously around its circumference between points 19 and 22, which therefore define the width of this last sealing area.

The open end 11 of section 14 being made of material which is relatively thin compared to that of the section 14 in the vicinity of bore 15, and because of the notches 12 and channels 13, therefore is flexible, as compared to section 1. Accordingly, when one inserts the capsule into an amalgamator, for being shaken in a path which lies substantially on the cylinder axis of the portions 3 and 4, the contents of the capsule are flung from one end to the other of their chambers. When this occurs, the inertial force of the mercury striking the end of chamber 7 defined by transition portion 16 and the next adjacent part of end 11, (that part to the right of point 18, FIG. 1), flexes some of end 11 toward the cylindrical axis of section 3, thereby providing a passageway between points 17 and 18 and the there normally-contacting adjacent outer surface of end 11 and the inside of bore 15. In reality, the flexing occurs substantially instantaneously in that when the mercury opens up the aforesaid passageway (not shown, as it is of indeterminate form) it escapes therethrough and into bore 15, and thereafter any flexed part of end 11, due to the inherent elasticity of the material, returns to sealing contact with the adjacent surface of bore 15, beforeth displacement which flung the mercury against transition portion 16 and flexible end 11 is followed by the next displacement, which could otherwise fling mercury toward end 11. Transition section 16 is champered at 17 to facilitate passage of mercury.

Looking at the sealed area between 17 and 18 as a passageway controlled by a normally-closed valve it will be seen that the valve' actuator is, in effect, transition 16 and end 11, and the area of the place or places struck by the mercury on end 11, convert the impact of the mercury into valve-opening force which flexes end 11 inwardly against a restoring force provided by the natural elasticity of the end, as determined by its dimensions, material, and form, including the notches and channels.

Once it has entered bore 15, which is actually one end of the chamber 8 which it closes, the mercury is confined to chamber 8, as in chamber 8, end 11 has no part which could act to flex it inward in response to the impact thereon of mercury in chamber 8. Moreover, once out of the relatively narrow confines of chamber 7, the mercury breaks up into many small globules and, along with the metal powder, forms a sort of dispersion the kinetic energy of which is mainly absorbed by the ends of chamber 8, which are provided by the rather robust end portions 10 and 14.

The operation of the valve is substantially instantaneous, for all practical purposes, and occurs practically immediately upon the beginning of shaking. In other words, the time necessary for proper amalgamation does not have to take into account the very short time interval between setting the capsule into motion and entry of the mercury into bore 15.

The use of a pestle will improve trituration time, so, all in all, we prefer that the capsule of the invention have a pestle therein. However, it nonetheless remains that the capsule according to the invention produces an amalgam of good characteristics in a reasonable trituration time, using a conventional amalgamator, i.e., a capsule-shaking machine, which oscillates the capsule at a frequency on the order of 1000 Hz.

In practice, the capsules, without pestles, will triturate to a commonly desired end point in about 5–40 seconds depending on the amalgamator, the amalgam formulation, and the number of "spills". With pestles, that end point is reached in not more than about 15 seconds, relatively independent of the amalgamator.

The exact shape and mass of the pestle are not critical. However, it is desirable to avoid smooth shapes, like spherical, as this leads to "wrap around", i.e., the amalgam may encapsulate a spherical pestle, and so would have to be peeled off by the dentist. In any event, a plastic disc (or portion thereof) such as shown in FIGS. 4a–f of Allet-Coche U.S. Pat. No. 3,809,225 would be suitable.

Figure 8:
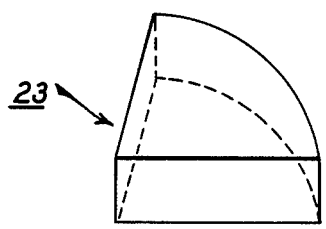
FIG. 8 is a perspective view of a pestle according to the invention.

In FIG. 8, we show an example of a suitable pestle form, namely, a sector 23 amounting to one-quarter of a full right-circularly cylindrical plastic disc as taught by Allet-Coche. Alternatively, the sector could be one-half of the full disc, and still be operative for the purpose indicated above.

The capsule according to our invention will normally be supplied to the dentist all ready charged with mercury and metal powder, so that to use it all he need do is take it out of a box or other storage means, insert it in any one of a variety of amalgamator machines now in use, and set the machine to shaking it for a time depending on the composition of the metal powder (usually one of several alloys), on his preferences in amalgam texture, and/or the number of "spills" in the capsule.

The concentric form of chamber 7 and 8 provides an axial symmetry suitable for forming the capsule pieces by conventional molding process. However, the chambers could be side by side, or, in any event, chamber 7 need not extend all the way around the section 9. As is known, the volume of chamber 9 depends on the quantities of amalgam components, and its length, on the kinetics of the amalgamator. The volume of chamber 7, as shown, is rather more generous than necessary just to contain the mercury, because the length of it shown has been found to be sufficient to develop sufficient inertia force from the mercury to actuate the valve.

Figure 7:
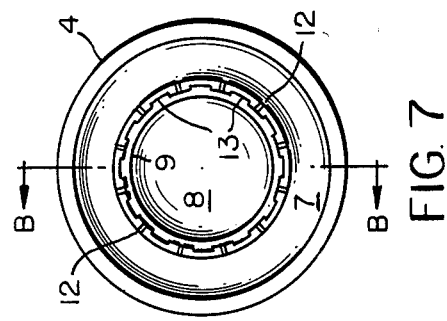
FIG. 7 is a left-end view of the capsule section of FIGS. 4 and 5.
Figure 4:
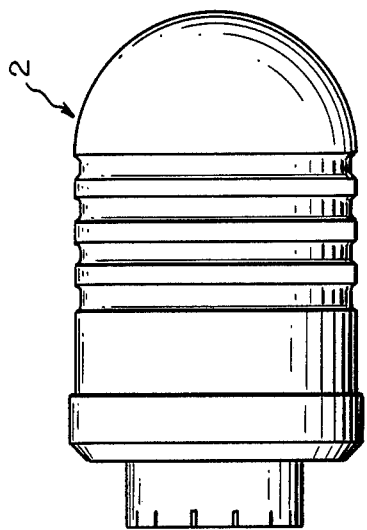
FIG. 4 is an elevation of the other section alone of the capsule and FIG. 5 is a sectional view thereof on the line B—B of FIG. 7.
Figure 5:
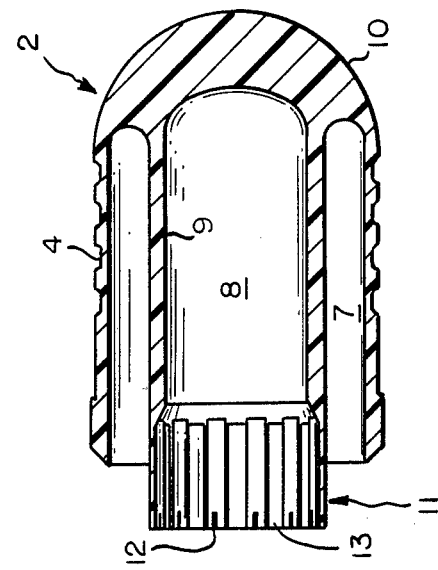
Figure 2:
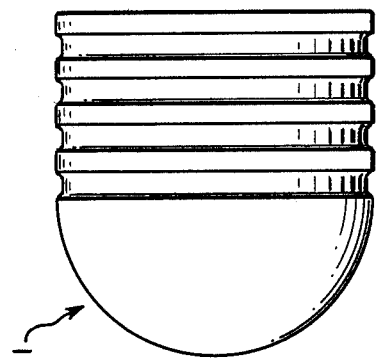
FIG. 2 is an elevation of one section alone of the capsule.
Figure 3:
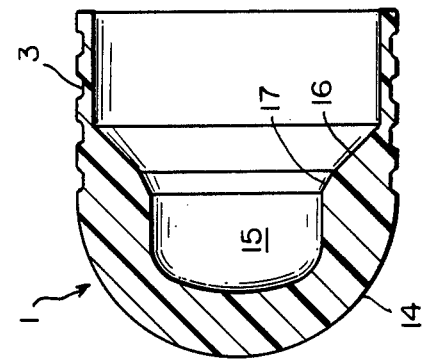
FIG. 3 is a sectional view thereof on the line A—A of FIG. 6.

Because the mercury tends to collect at the lowest point in chamber 7, when the capsule is used in an amalgamator having horizontally directed shaking motion, corresponding portions of end 11 and transition section 16 will be acted on by substantially a unitary body of mercury. The same result would be achieved the chamber 7 was a simple tubular bore of the length shown in FIG. 7, and alongside chamber 8 and having a diameter of about the radial distance between section 9 and portion 4.

It will be observed that the mercury if concentrated in a unitary body will flex only a minor portion of end 11. Again, the molding process makes it convenient to make the end 11 capable of flexing at any place on its circumference.

The material of the capsule can be polyethylene, a "hard" form being desirable for piece 1 and a medium "hard" form being desirable for piece 2. Using sufficiently dense material reduces the chance of contamination between chambers. Tolerances for the fit between the two capsules are required to be such as to prevent leakage of mercury out of chamber 7. A preferred set of dimensions would be those including a longest dimension of 3.35 cm for the assembled version as shown in FIG. 1.

It will be seen from the foegoing that our novel capsule provides the utmost of economy, ease, and simplicity of manufacture, charging and use, as compared to the prior art capsules referred to above.

Therefore, having described our invention in accordance with 35 USC 112, We claim:

1. A capsule for containing in unmixed condition the components of a dental amalgam, said capsule having a mixing chamber, said chamber being provided by wall means, said wall means enclosing a space in said capsule such as to provide a surface which bounds said space and defines a mixing chamber shaped and dimensioned for mixing said components, if said components be present in said chamber while said capsule is being shaken;

said wall means also providing a mercury chamber for containing mercury, both said chambers being normally closed off from each other, with the mercury chamber containing mercury and said mixing chamber containing dental alloy, and there being sufficient space in said mercury chamber that if said capsule be shaken, said mercury strikes a place on said wall means and thereby exerts inertial force on said wall means at said place;

said wall means having valve means responsive to said force for deflecting a portion of said wall means into said chamber, such deflection altering the original shape of said surface while at the same time providing a way for mercury to both enter into said mixing chamber through said valve means and cease exerting said inertial force on said wall means at said place, said valve means being responsive to such cessation of exerting said inertial force for causing said portion of said wall means to deflect such as to restore said chamber to its said original shape.

2. The capsule of claim 1, wherein said mixing chamber has a pestle therein.

3. The capsule of claim 2, wherein said wall means are defined by first and second cylindrical walls, the former surrounding the latter for defining said mercury chamber as space between said walls therebetween, said valve means being in the form of a resilient portion of said second wall, said resilient portion being so located that if said capsule be shaken along its length, and there be said quantity of mercury in said space between said walls, said mercury will be propelled back and forth therein and strike said resilient portion and by its inertial force open said valve means and pass therethrough into the space in said second wall.

4. The capsule of claim 3, wherein said mixing chamber has a pestle therein.

5. The capsule of claim 4 wherein said valve means opens by deflecting said resilient portion away from said first wall and closes by deflecting said resilient portion back to said first wall.

6. The capsule of claim 5, wherein said mixing chamber has a pestle therein.

7. A capsule consisting of a first and second section, said capsule having a first chamber therein for containing a given quantity of alloy and being shaped and dimensions such that if a suitable quantity of mercury be introduced to said first chamber and the presence of said quantity of alloy, and the said capsule be shaken in a certain manner, and said mercury and alloy will be propelled back and forth between opposite ends of said first chamber, said first section having a bore therein, said second section having a second chamber therein, for containing said quantity of mercury and being shaped and dimensions such that if said capsule be shaken in said manner, said quantity of mercury, if present in said second chamber, will be propelled back and forth between and against places on opposite ends of said second chamber, said second section also having said first chambers therein, said first chamber opening directly into said bore, said capsule having normally closed valve means for allowing said mercury to be propelled into said first chamber when said valve means is open, said valve means including one of said places; and said one of said places having means responsive to initial force of said mercury for opening said valve means when said mercury is present in said second chamber and is propelled against said one of said places when said capsule is shaken as aforesaid, said valve means including a portion of said first section and a portion of said second section sealing and engaging each other, and sealing said second chamber off from said bore, the second said portion having a surface providing said one of said places, and being responsive to said force such as to flexibly disengage from the first said portion so as to provide said valve means, said second chamber being annular and surrounds said first chamber so that a common wall separates said chambers, said common wall providing said second set portion.

8. The capsule of claim 7 wherein said bore has a frusto-conical section surrounding said common wall and a cylindrical section, said common wall goes through said frusto-conical section and sealingly engages the surface of said cylindrical section, said second said portion being surround with said frusto-conical section.

9. The capsule of claim 7 wherein alloy and mercury, respectively, are in said first and second chambers, and one of said chambers has a pestle therein.

10. The capsule of claim 7 wherein alloy and mercury, respectively, are in said first and second chambers, and said first chamber has a pestel therein.

* * * * *